United States Patent
Teepe et al.

(10) Patent No.: US 11,519,894 B2
(45) Date of Patent: Dec. 6, 2022

(54) OPTICAL MONITORING TO DETECT CORROSION OF POWER GRID COMPONENTS

(71) Applicants: Palo Alto Research Center Incorporated, Palo Alto, CA (US); Consolidated Edison Company of New York, Inc., New York, NY (US)

(72) Inventors: Mark Teepe, Menlo Park, CA (US); Todd Karin, Fairfield, CA (US); Peter Kiesel, Palo Alto, CA (US); Ajay Raghavan, Mountain View, CA (US); Jane Shin, New York, NY (US); Bradley Kittrell, New York, NY (US); Serena Lee, New York, NY (US)

(73) Assignees: Palo Alto Research Company Incorporated, Palo Alto, CA (US); Consolidated Edison Company of New York, Inc., New York, NY (US)

( * ) Notice: Subject to any disclaimer, the term of this patent is extended or adjusted under 35 U.S.C. 154(b) by 69 days.

(21) Appl. No.: 17/151,377

(22) Filed: Jan. 18, 2021

(65) Prior Publication Data
US 2021/0239675 A1 Aug. 5, 2021

Related U.S. Application Data

(63) Continuation of application No. 16/662,726, filed on Oct. 24, 2019, now Pat. No. 10,895,566.

(51) Int. Cl.
*G01N 33/2045* (2019.01)
*G01D 5/26* (2006.01)
*G01R 31/62* (2020.01)

(52) U.S. Cl.
CPC ......... *G01N 33/2045* (2019.01); *G01D 5/268* (2013.01); *G01R 31/62* (2020.01)

(58) Field of Classification Search
CPC .... G01N 33/2045; G01N 17/04; G01D 5/268; G01D 5/35316; G01R 31/62
See application file for complete search history.

(56) References Cited

U.S. PATENT DOCUMENTS 2,976,123 A * 3/1961 Marsh .................... G01N 17/00
422/53
5,499,313 A 3/1996 Kleinerman
(Continued)

FOREIGN PATENT DOCUMENTS

CN 201892586 7/2011
CN 202221693 6/2012
(Continued)

OTHER PUBLICATIONS

European Extended Search Report from EP Application No. 20199480.3 dated May 7, 2021, 11 pages.
(Continued)

*Primary Examiner* — Roy M Punnoose
(74) *Attorney, Agent, or Firm* — Mueting Raasch Group

(57) ABSTRACT

A corrosion monitoring system includes one or more objects coupled to respective portions of a transformer tank. The one or more objects are configured to corrode before the respective portions of the transformer tank. At least one optical sensor is coupled to each of the objects. The at least one optical sensor has an optical output that changes in response to strain of the object. An analyzer is coupled to the at least one optical sensor. The analyzer is configured to perform one or more of detecting and predicting corrosion of the transformer tank based on the output of the at least one optical sensor.

20 Claims, 6 Drawing Sheets

(56) References Cited

U.S. PATENT DOCUMENTS

| | | | |
|---|---|---|---|
| 7,843,298 B2 | 11/2010 | Hosokawa et al. | |
| 7,845,404 B2 | 12/2010 | McStay et al. | |
| 8,345,264 B2* | 1/2013 | Huang | G01D 5/268 |
| | | | 356/600 |
| 9,664,609 B2* | 5/2017 | Magne | G01N 17/04 |
| 10,215,916 B2 | 2/2019 | Iwakawa | |
| 10,895,566 B1* | 1/2021 | Teepe | G01N 17/04 |
| 2007/0019898 A1 | 1/2007 | Chimenti et al. | |
| 2009/0135427 A1* | 5/2009 | Huang | G01N 21/55 |
| | | | 356/445 |
| 2014/0092375 A1* | 4/2014 | Raghavan | H01M 10/48 |
| | | | 356/32 |
| 2014/0321799 A1* | 10/2014 | Udd | G02B 6/022 |
| | | | 385/13 |
| 2017/0356870 A1 | 12/2017 | Doany et al. | |
| 2019/0011491 A1* | 1/2019 | Raghavan | G01J 3/00 |
| 2019/0317130 A1 | 10/2019 | Sun et al. | |
| 2021/0148832 A1* | 5/2021 | Kvryan | G01N 17/04 |
| 2022/0057279 A1* | 2/2022 | Kumar | G01M 5/0091 |

FOREIGN PATENT DOCUMENTS

| | | | |
|---|---|---|---|
| CN | 101949744 | 8/2012 | |
| CN | 108151910 | 6/2018 | |
| EP | 0646304 | 4/1995 | |
| EP | 2388357 A2 * | 11/2011 | C23F 13/06 |

OTHER PUBLICATIONS

Greene et al., "Grating-based optical fiber corrosion sensors" Proceedings of SPIE, Smart Structures and Materials 97, Jun. 6, 1997, 8 pages.

Handawi et al., "Strain based FBG sensor for real-time corrosion rate monitoring in pre-stressed structures", Sensors and Actuators 236, 2016, pp. 276-285.

Lee et al., "A structural corrosion-monitoring sensor based on a pair of prestrained fiber Bragg gratings", Meas. Sci. Technol., 21, 2010, 7 pages.

Cinitha et al., "Inspection Techniques for Damage Detection in Civil Engineering Structures of Low Carbon Steel in a Corrosive Environment Using Fiber Bragg Technology", Construction and Building Materials 217, 2019, pp. 265-272.

Hegyi et al., "Time- and Wavelength-Multiplexed Wavelength Shift Detection for High-Resolution, Low-Cost Distributed Fiber-Optic Sensing," J. Lightwave Technol. 35, 2017, pp. 4234-4241.

Hoffman et al., "The No-U-turn sampler: adaptively setting path lengths in Hamiltonian Monte Carlo." Journal of Machine Learning Research 15.1, 2014, pp. 1593-1623.

Lisowska-Lis, "Thermographic monitoring of the power transformers." Measurement Automation Monitoring 63, 2017.

Utami et al. "Evaluation condition of transformer based on infrared thermography results." Properties and Applications of Dielectric Materials, 2009, IEEE 9th International Conference on the. IEEE, 2009.

* cited by examiner

OPTICAL MONITORING TO DETECT CORROSION OF POWER GRID COMPONENTS

RELATED APPLICATIONS

This application is a continuation of U.S. patent application Ser. No. 16/662,726, filed Oct. 24, 2019, to which priority is claimed pursuant to 35 U.S.C. § 119(e), and which is incorporated herein by reference in its entirety.

STATEMENT REGARDING FEDERALLY SPONSORED RESEARCH AND DEVELOPMENT

This invention is based on work supported by the U.S. Department of Energy (DOE)/Office of Electricity through the DOE National Energy Technology Laboratory under award agreement #DE-OE0000872. The Government has certain rights to this invention.

TECHNICAL FIELD

This application relates generally to techniques for optically monitoring power grid transmission and distribution systems. The application also relates to components, devices, systems, and methods pertaining to such techniques.

BACKGROUND

Global climate change and population growth are driving increased demands for reliable, sustainable, and clean electricity around the world. This is creating an even heavier burden on the already overstressed and aging global power infrastructure. Modern power grids are complex, tightly interconnected systems. Certain extraneous conditions at key locations can have unpredictable and immediate impacts over a wide area. The existing power grid suffers from a lack of effective distributed communications, monitoring, fault diagnostics, and automation, which further increase the possibility of wide-area breakdown due to cascading effects from a single fault.

SUMMARY

Embodiments described herein involve a corrosion monitoring system comprising: one or more objects coupled to respective portions of a transformer tank. The one or more objects are configured to corrode before the respective portions of the transformer tank. At least one optical sensor is coupled to each of the objects. The at least one optical sensor has an optical output that changes in response to strain of the object. An analyzer is coupled to the at least one optical sensor. The analyzer is configured to perform one or more of detecting and predicting corrosion of the transformer tank based on the output of the at least one optical sensor.

A method for monitoring corrosion involves sensing, via one or more optical sensors, one or more strain values of one or more objects coupled to a transformer tank. Corrosion of the transformer tank is monitored based on the one or more strain values.

The above summary is not intended to describe each embodiment or every implementation. A more complete understanding will become apparent and appreciated by referring to the following detailed description and claims in conjunction with the accompanying drawings.

BRIEF DESCRIPTION OF THE DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
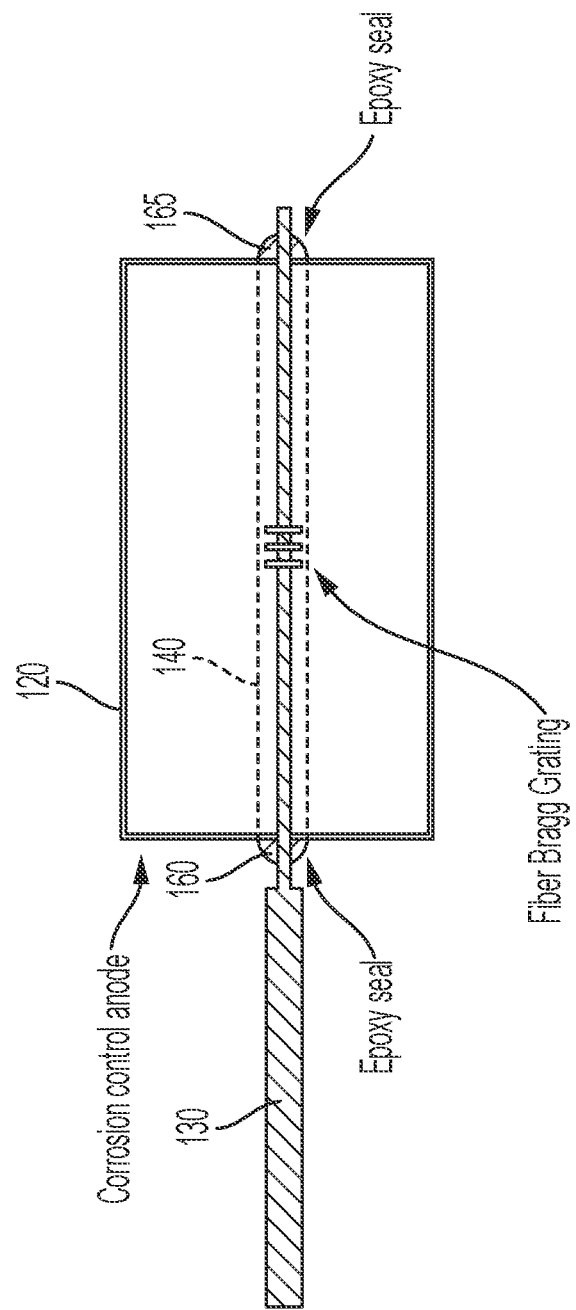
FIG. 1 shows using an optical sensor to measure a corrosion state of an anode in accordance with embodiments described herein.

Fluid-filled grid assets such as transformers are used across the electrical grid. The fluid may be mineral oil or ester, for example. The fluid is used both for its dielectric strength (to allow a more compact build) and for its heat transfer ability. The heat transfer is used to keep the working electrical features at a lower temperature by providing thermal conductivity to the exterior tank wall. The heat is dissipated into the surrounding fluid and transferred to the tank and radiator walls in two ways: 1) direct heat conduction through the liquid; and 2) heat convection between the circulated fluid and tank walls. The heat is then dissipated into environment through the highly emissive radiator surface, via radiation and convection. Often a "radiator" element can be used in order to increase the heat transfer rate from the tank to the environment.

Heat transfer to the environment may be impeded in multiple ways. The exterior wall of the asset may be designed/painted with a material with a high emissivity and corrosion resistance. The high emissivity material increases the heat transfer rate from the tank to the environment. If this material is corroded or contaminated, the heat transfer rate is lowered. This will also affect the fluid circulation rate and in turn change the temperature distribution trends inside the tank. Thus, by measuring a fine gradient of temperature points inside the asset, it is possible to detect soiling, degradation or debris on the outside of the asset. Thermography may be used as a sensing methodology through infrared sensors for monitoring temperatures due to most direct sensing methods being either too costly or simply unable to withstand the harsh environments of transformer tanks, for example. Techniques using thermography tend to focus primarily on the issues involving the deteriorated electrical insulation and not those of the exterior wall's degradation. While thermography may provide invaluable insight on the thermal conditions inside a tank transformer, it is not suitable for continuous monitoring purposes that exterior surface monitoring applications use.

A high percentage of network transformer failures are due to corrosion and/or other contamination of the transformer tank. The degree of corrosion and/or contamination taking place is also difficult to quantify by visual inspection making predictive failure difficult. Exterior contamination can be highly destructive and dangerous to the transformer's health, especially for assets in underground vaults. Typically, these vaults are concrete vaults underneath a city and/or town street with a grate on a sidewalk or roadway where material from the city street can enter. Since these gratings allow significant amounts of corrosive materials to the exterior of the tank, it may be desirable to monitor the degree of soiling, contamination and/or debris on the outside of the asset.

Currently, exterior contamination may not be directly measured. In the harsh exterior environments where external corrosion and debris accumulation is inevitable, exterior sensors may have a low chance of survival for extended periods of time. To account for this, if an electrical asset is flagged for inspection, operators may clean the exterior of the asset during the visit. Embodiments described herein provide a means to remotely monitor the amount of contamination and/or corrosion occurring in the transformer vault in real time so that action can be taken before a major failure occurs.

Embodiments described herein may involve a way to utilize the properties of fiber Bragg gratings (FBGs) to monitor the degree of corrosion occurring inside a network transformer tank. This would provide a way to predict when transformer failure due to corrosion might occur. The transformer tank itself is basically a large metal container which houses the transformer coils and is almost completely filled with oil. Corrosion of this tank metal can occur over time when it reacts with the surrounding environment to form a new compound, typically an oxide of the base metal. This conversion process is normally accompanied by a volume change as the original metal is converted into a less dense oxide. It is the strain associated with this volume change that we can detect and measure with properly implemented FBGs.

In relatively large structures such as transformer tanks, corrosion can occur anywhere along the surface leading to some areas that are more severely corroded than others. This makes it very difficult to determine when a hole or crack has occurred in one section of the tank leading to oil leakage and failure. Rather than trying to cover the entire surface of the tank with sensors, a more elegant approach is to monitor the corrosion occurring in the corrosion control anodes. Corrosion control anodes are used to mitigate transformer corrosion through a technique known as cathodic protection. In this technique a more easily corroded material, also called the anode, is placed in contact with the metal that one is trying to protect. This "sacrificial anode", is then preferentially corroded and provides a degree of corrosion resistance to the metal one is trying to protect, much like a galvanic cell. In some configurations, these anodes are blocks of magnesium or zinc that are placed on or around the transformer and are electrically connected to the tank itself. By measuring the strain generated in these anodes over time the progression of the corrosion process can be monitored. A correlation between the corrosion of the anode and the tank metal can be established such that measuring the anode will provide an indication of the corrosion state of the tank.

One example of how an FBG can be implemented to measure the corrosion state of the anode is shown in FIG. 1. Here, a cavity 140 has been drilled into the bulk of the anode 120 and an FBG 130 inserted into the cavity 140. Both ends of the FBG 130 are fixed to the anode 120 with epoxy 160, 165 to provide translation of the bulk strain in the anode 120 to the FBG 130. The epoxy 160, 165 also serves to seal up the cavity 140 to prevent corrosion of the anode 120 from within. According to embodiments described herein, at least one end 160, 165 of the FBG 130 should be fixed first and then strain applied while the other side is curing to provide pre-tension to the FBG 130. This improves the sensitivity of the strain measurement by removing any slack in the fiber. Oxidation of the anode will begin at the surface and work its way into the bulk creating strain due to the expansion of the oxidized portions of the anode. When the anode is fully consumed, a release of the pre-strain will occur giving confirmation that the anode needs to be replaced. According to embodiments described herein, when the anode is consumed, it no longer provides corrosion resistance to the tank metal.

According to embodiments described herein, the anode comprises a material that is configured to corrode more quickly than the material of the transformer tank. One or more additional anodes that are the same and/or a similar material as the transformer tank may be used to offer a comparison to the sacrificial anode. This additional anode may or may not be electrically coupled to the transformer tank and would not provide any corrosion resistance but would serve as an additional data point to aid in the predictive model.

Figure 2A:
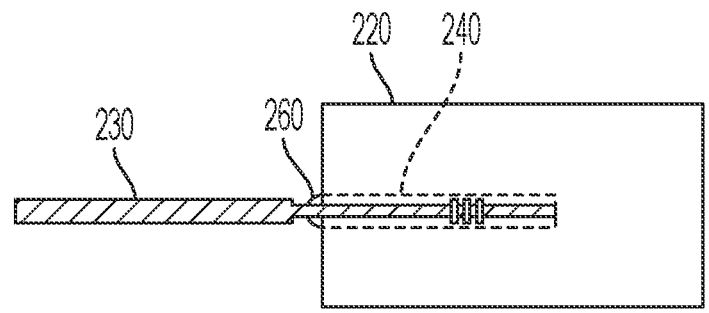
FIGS. 2A-2C illustrate different configurations for measuring a corrosion state of an anode using one or more optical sensors in accordance with embodiments described herein.

While FIG. 1 shows an example of using a single FBG to measure a corrosion state of an anode, it is to be understood that other configurations could be implemented. For example, FIG. 2A shows an example in which the cavity 240 is drilled through only a portion of the anode 220. Thus, the FBG 230 is only disposed through a portion of the anode 220. In this example, an epoxy seal 260 is used at only one end of the FBG 230.

Figure 2B:
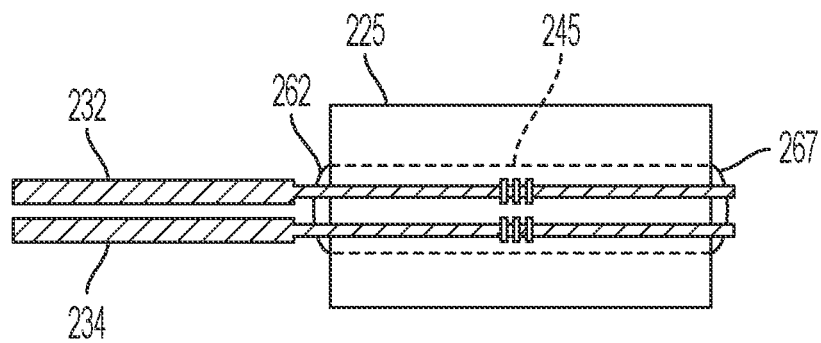
Figure 2C:
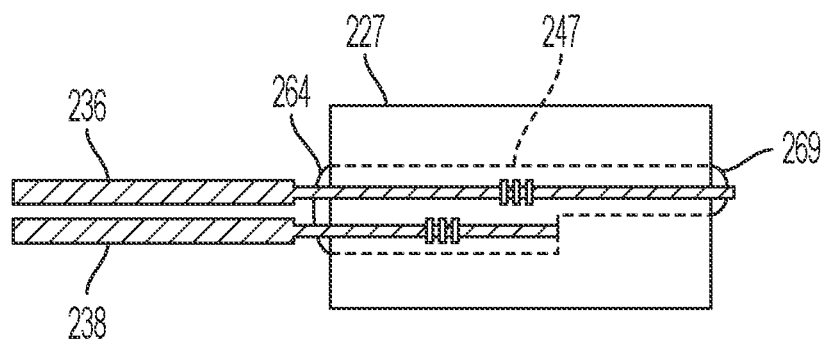

According to various embodiments described herein, multiple fibers could also be inserted into the same anode in various configurations and/or depths to provide more accurate tracking of how the corrosion is progressing. FIGS. 2B and 2C show examples having multiple FBGs inserted into an anode. Specifically, FIG. 2B shows an example in which two FBGS 232, 234 are inserted into a cavity 245 in the same anode 225. Here, the two FBGs 232, 234 are both inserted all the way through the anode 225. An epoxy seal 262, 267 is disposed on both sides of the FBGs 232, 234. FIG. 2C shows another example having two FBGs 236, 238 inserted into a cavity 247 of a single anode 227. Here, a first FBG 1036 is inserted all the way through the anode 227 and has an epoxy seal 264, 269 on both ends. A second FBG 238 is disposed through only a portion of the anode 227 and has an epoxy seal 264 at the exposed end. Since FBGs are also very sensitive temperature sensors, is may be helpful to separate the temperature effects from the corrosion induced strain. This may be accomplished by subtracting out the signal from a separate FBG that is not affected by the anodic strain but is subject to the same temperature environment as the strain sensor. This temperature correcting fiber can be placed anywhere nearby or even in the same cavity as the strain sensor with only one end fixed so it is not affected by anodic corrosion. Therefore, the second FBG shown in 238 may be configured as a temperature correcting fiber.

Figure 3:
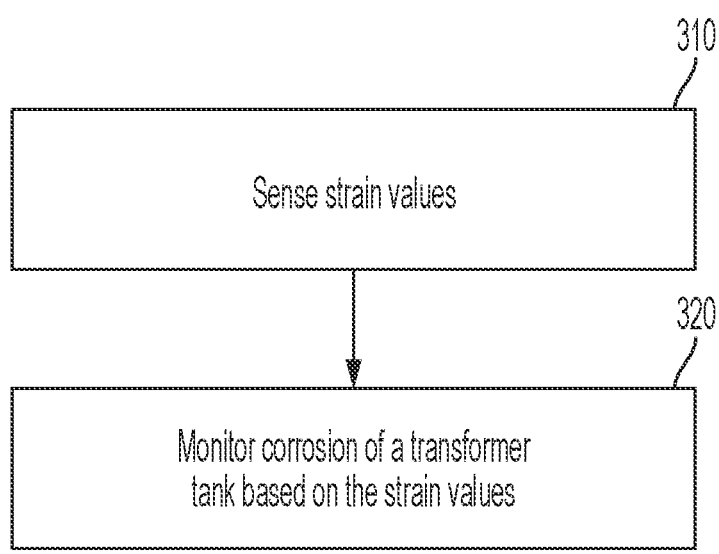
FIG. 3 illustrates a process for predicting corrosion of a transformer tank using an FBG inserted into an object associated with the transformer tank in accordance with embodiments described herein.

FIG. 3 illustrates a process for predicting corrosion of a transformer tank using an FBG inserted into an object associated with the transformer tank in accordance with embodiments described herein. One or more strain values of one or more objects coupled to a transformer tank are sensed 310 via one or more optical sensors. Corrosion of the transformer tank is monitored 320 based on the one or more strain values. The corrosion may be monitored continuously in embodiments described herein.

Figure 4A:
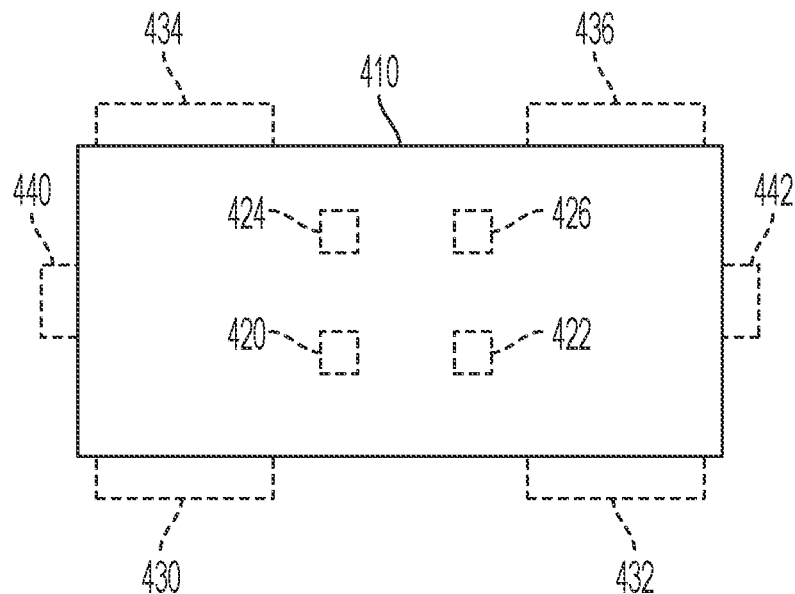
FIGS. 4A and 4B show examples of possible anode locations on a transformer tank in accordance with embodiments described herein.
Figure 4B:
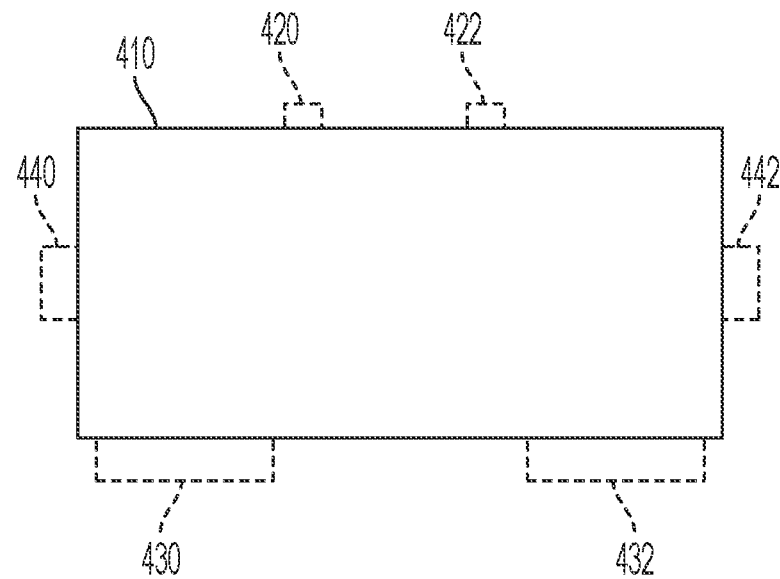

FIGS. 4A and 4B show examples of possible anode locations on a transformer tank in accordance with embodiments described herein. FIG. 4A illustrates a top view of a transformer tank 410 and FIG. 4B illustrates a side view of the same transformer tank 410. Possible locations for top anodes 420, 422, 424, 426, bottom anodes 430, 432, 434, 1236, and side anodes 440, 442 are shown. While a specific number of anodes are shown for each of these sides of the transformer tank 410, it is to be understood that more or fewer anodes may be disposed on any respective side of the transformer tank 410. Each of the anodes may be disposed directly on the transformer tank in some embodiments. In some configurations, one or more of the anodes may be disposed a distance away from the transformer tank and connected to the tank via a wire, for example.

EXAMPLE

Figure 5:
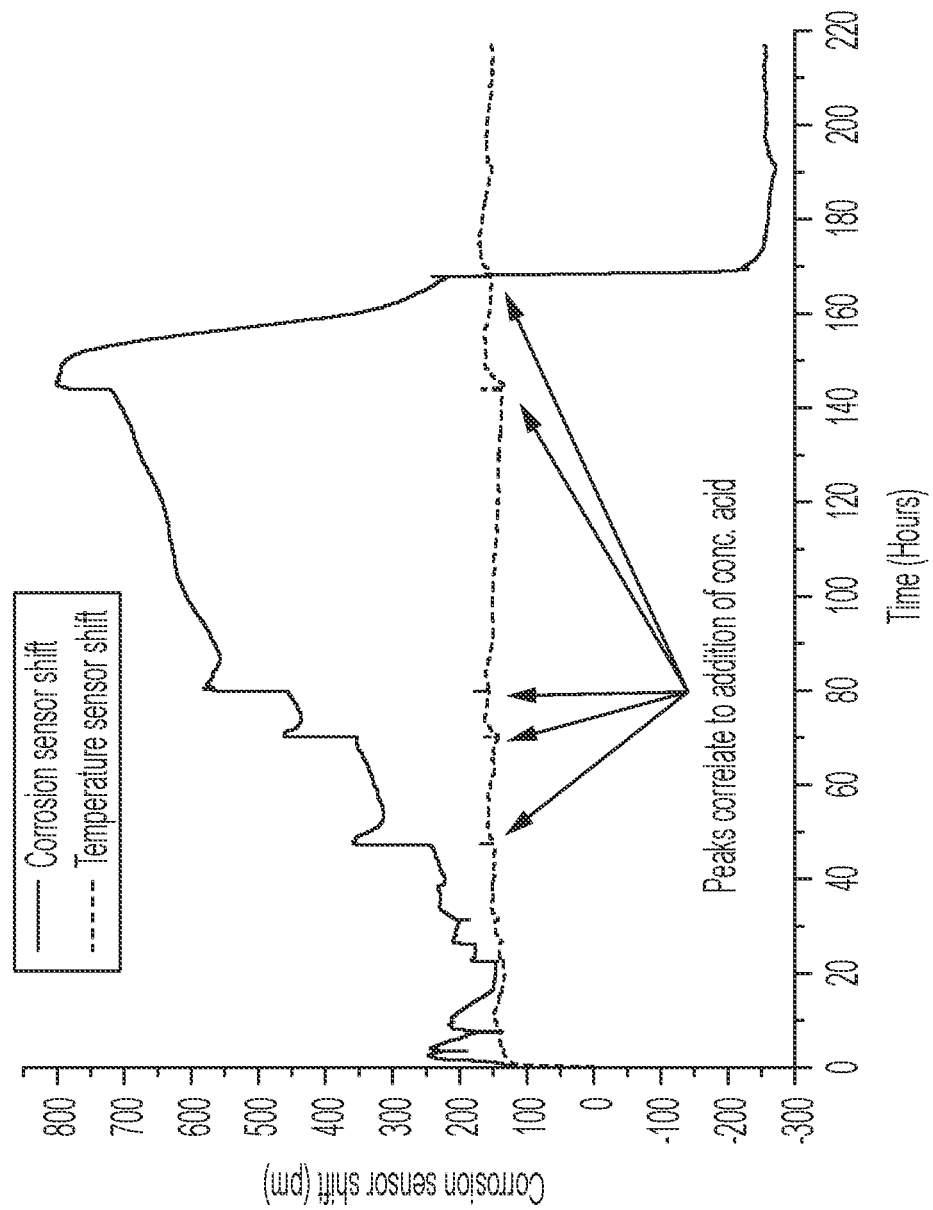
FIG. 5 shows the shift in the reflected peak of the FBG as a function of time in accordance with embodiments described herein.

An FBG was embedded in a block of steel with the configuration displayed in FIG. 1. This sample was subjected to accelerated corrosion in a bath of dilute $HNO_3$ using a second FBG as temperature compensation. FIG. 5 shows the shift in the reflected peak of the FBG as a function of time. This peak shift is a direct result of the stretching of the FBG due to expansion of the steel block undergoing corrosion. The peak shift gets larger over time indicating continual corrosion up to the point where the block has been nearly consumed and the fiber tension is released. In this experiment additional acid was added at various times which clearly caused peaks in the corrosion and temperature signals. Adding acid to the bath increases the corrosion rate and the temperature spikes very quickly. The data clearly shows the ability to observe corrosion occurring in real time.

Figure 6:
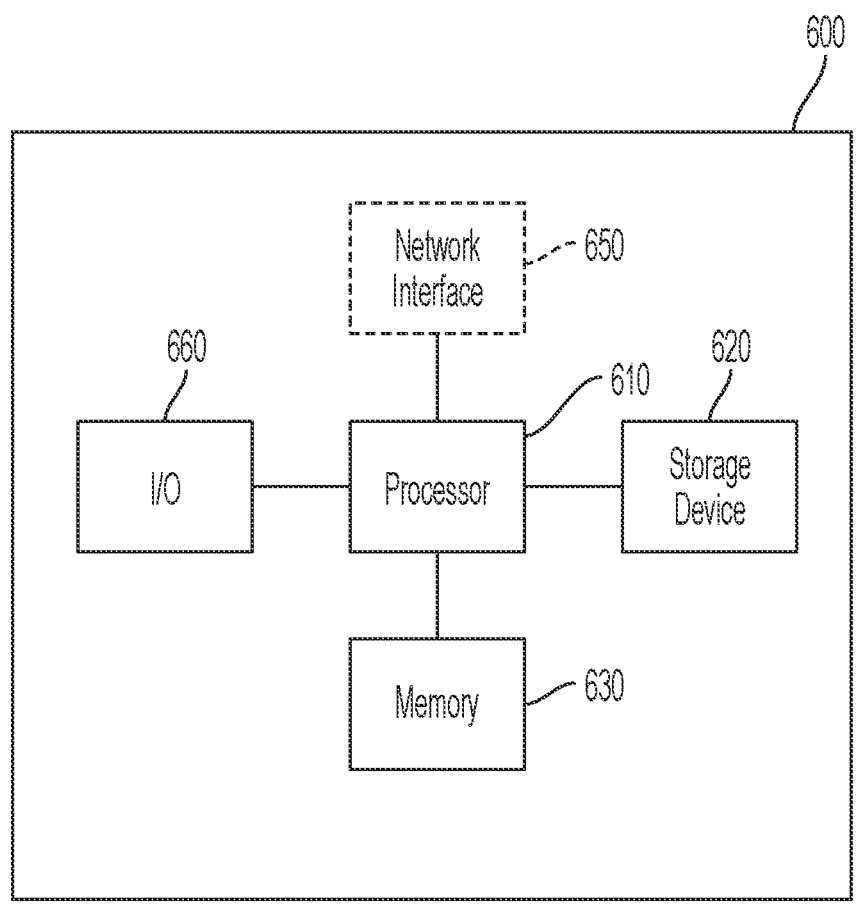
FIG. 6 shows a block diagram of a system capable of implementing embodiments described herein.

The above-described methods can be implemented on a computer using well-known computer processors, memory units, storage devices, computer software, and other components. A high-level block diagram of such a computer is illustrated in FIG. 6. Computer 600 contains a processor 610, which controls the overall operation of the computer 600 by executing computer program instructions which define such operation. It is to be understood that the processor 610 can include any type of device capable of executing instructions. For example, the processor 610 may include one or more of a central processing unit (CPU), a graphical processing unit (GPU), a field-programmable gate array (FPGA), and an application-specific integrated circuit (ASIC). The computer program instructions may be stored in a storage device 620 (e.g., magnetic disk) and loaded into memory 630 when execution of the computer program instructions is desired. Thus, the steps of the methods described herein may be defined by the computer program instructions stored in the memory 630 and controlled by the processor 610 executing the computer program instructions. According to embodiments described herein, the computer 600 may perform method steps as part of a server or cloud-based service. The computer 600 may include one or more network interfaces 650 for communicating with other devices via a network. The computer 600 also includes other input/output devices 660 that enable user interaction with the computer 600 (e.g., display, keyboard, mouse, speakers, buttons, etc. FIG. 6 is a high level representation of possible components of a computer for illustrative purposes and the computer may contain other components.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The various embodiments described above may be implemented using circuitry and/or software modules that interact to provide particular results. One of skill in the computing arts can readily implement such described functionality, either at a modular level or as a whole, using knowledge generally known in the art. For example, the flowcharts illustrated herein may be used to create computer-readable instructions/code for execution by a processor. Such instructions may be stored on a computer-readable medium and transferred to the processor for execution as is known in the art.

The foregoing description of the example embodiments have been presented for the purposes of illustration and description. It is not intended to be exhaustive or to limit the inventive concepts to the precise form disclosed. Many modifications and variations are possible in light of the above teachings. Any or all features of the disclosed embodiments can be applied individually or in any combination, not meant to be limiting but purely illustrative. It is intended that the scope be limited by the claims appended herein and not with the detailed description.

What is claimed is:

1. A corrosion monitoring system, comprising:
one or more objects coupled to respective portions of a grid asset, the one or more objects configured to corrode before the respective portions of the grid asset;
at least one optical sensor coupled to each of the objects, the at least one optical sensor having an optical output that changes in response to strain of the object; and
an analyzer coupled to the at least one optical sensor, the analyzer configured to perform one or more of detecting and predicting corrosion of the grid asset based on the output of the at least one optical sensor.

2. The corrosion monitoring system of claim 1, wherein the analyzer is configured to detect a change in volume of the one or more objects based on the optical output.

3. The corrosion monitoring system of claim 2, wherein the change in volume is caused by a decrease in density of the one or more objects.

4. The corrosion monitoring system of claim 2, wherein the analyzer is configured to predict corrosion based on the detected change in volume.

5. The corrosion monitoring system of claim 1, wherein the grid asset comprises a fluid-filled grid asset.

6. The corrosion monitoring system of claim 5, wherein the fluid-filled grid asset comprises a transformer.

7. The corrosion monitoring system of claim 1, wherein at least one of the one or more objects is a sacrificial anode.

8. The corrosion monitoring system of claim 1, wherein at least one of the one or more objects is disposed proximate a radiator of the grid asset.

9. The corrosion monitoring system of claim 1, wherein at least one of the at least one optical sensor comprises a fiber Bragg grating (FBG).

10. The corrosion monitoring system of claim 1, wherein the analyzer is configured to continuously predict corrosion of the grid asset based on the output of the at least one optical sensor.

11. The corrosion monitoring system of claim 1, further comprising at least one additional optical sensor having an optical output that changes in response to a temperature of the object and is not sensitive to strain.

12. The corrosion monitoring system of claim 11, wherein the analyzer is configured to predict corrosion of the grid asset based on the output of the at least one optical sensor and the at least one additional optical sensor.

13. The corrosion monitoring system of claim 11, wherein the analyzer is configured to predict corrosion of the grid asset by subtracting the output of one of the at least one additional sensor from the output of one of the at least one optical sensor.

14. The corrosion monitoring system of claim 13, wherein the one additional sensor is disposed proximate to the at least one optical sensor.

15. The corrosion monitoring system of claim 1, wherein the object comprises a cavity and the at least one optical sensor is disposed within the cavity.

16. The corrosion monitoring system of claim 15, wherein the at least one optical sensor coupled to each of the objects comprises a first optical sensor and a second optical sensor, the first optical sensor having one or more of a different configuration and a depth within the cavity than the second optical sensor.

17. A method for monitoring corrosion, comprising:
sensing, via one or more optical sensors, one or more strain values of one or more objects coupled to a grid asset, the one or more objects configured to corrode before one or more portions of the grid asset; and
monitoring corrosion of the grid asset based on the one or more strain values.

18. The method of claim 17, wherein at least one of the at least one optical sensor comprises a fiber Bragg grating (FBG).

19. The method of claim 17, wherein the analyzer is configured to predict corrosion of the grid asset based on the output of the at least one optical sensor and at least one additional optical sensor having an optical output that changes in response to a temperature of the object and is not sensitive to strain.

20. The method of claim 19, further comprising predicting corrosion of the grid asset by subtracting the output of one of the at least one additional sensors from the output of one of the at least one optical sensors.

* * * * *